US008142594B2

(12) United States Patent
Hille et al.

(10) Patent No.: US 8,142,594 B2
(45) Date of Patent: Mar. 27, 2012

(54) METHOD FOR THE MULTI-TRACK TAILORING OF TRANSDERMAL THERAPEUTIC PATCHES

(75) Inventors: Thomas Hille, Koblenz (DE); Peter Steinborn, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 227 days.

(21) Appl. No.: 12/657,317

(22) Filed: Jan. 19, 2010

(65) Prior Publication Data
US 2010/0122765 A1 May 20, 2010

Related U.S. Application Data

(63) Continuation-in-part of application No. PCT/EP2008/006678, filed on Aug. 14, 2008.

(60) Provisional application No. 60/965,616, filed on Aug. 21, 2007.

(51) Int. Cl.
- B29C 65/48 (2006.01)
- B29C 65/52 (2006.01)
- B32B 37/02 (2006.01)
- B32B 37/26 (2006.01)
- B32B 38/04 (2006.01)
- B32B 38/10 (2006.01)

(52) U.S. Cl. ........ 156/247; 156/248; 156/249; 156/262; 156/263; 156/289

(58) Field of Classification Search .......... 156/247–250, 156/262, 263, 265, 289
See application file for complete search history.

(56) References Cited

U.S. PATENT DOCUMENTS

| | | | | |
|---|---|---|---|---|
| 2,372,617 A | * | 3/1945 | Trew | 156/252 |
| 2,789,640 A | * | 4/1957 | Belden | 53/435 |
| 3,574,026 A | * | 4/1971 | Kucheck | 156/152 |
| 3,620,880 A | * | 11/1971 | Lemelson | 156/384 |
| 3,707,422 A | * | 12/1972 | Helm | 156/511 |
| 4,556,441 A | * | 12/1985 | Faasse, Jr. | 156/247 |
| 4,592,753 A | * | 6/1986 | Panoz | 424/449 |
| 4,664,736 A | * | 5/1987 | Faasse, Jr. | 156/264 |
| 4,666,441 A | * | 5/1987 | Andriola et al. | 424/448 |
| 4,715,926 A | * | 12/1987 | Murasaki | 156/511 |
| 4,782,647 A | * | 11/1988 | Williams et al. | 53/454 |
| 4,789,415 A | * | 12/1988 | Faasse, Jr. | 156/519 |
| 4,991,378 A | * | 2/1991 | Dotta | 53/520 |
| 5,268,179 A | * | 12/1993 | Rudella | 424/449 |
| 5,405,486 A | * | 4/1995 | Sablotsky et al. | 156/510 |

(Continued)

FOREIGN PATENT DOCUMENTS
DE 44 05 296 C1 6/1995
(Continued)

*Primary Examiner* — Sing P Chan
(74) *Attorney, Agent, or Firm* — R. S. Lombard; K. Bach

(57) ABSTRACT

A method for the multi-track tailoring of transdermal therapeutic patches having at least a one-layer, adhesive reservoir foil containing an active ingredient, which is disposed between an adhesive back foil and a removable protective foil. The reservoir foils are applied per track with their adhesive layers on a transport element moving discontinuously in the longitudinal direction of the reservoir foils. After separating sections of the size of a patch or band aid the same are transferred to a further transport element that is moved continuously for depositing the same thereon in spaced relationship. The present invention provides a method for multi-track tailoring, wherein web-shaped reservoir foils, which can be unwound from rolls, may be utilized without producing any waste containing the active ingredient.

11 Claims, 4 Drawing Sheets

U.S. PATENT DOCUMENTS

| | | | |
|---|---|---|---|
| 5,492,590 A * | 2/1996 | Sakai | 156/701 |
| 5,656,285 A * | 8/1997 | Sablotsky et al. | 424/448 |
| 5,681,413 A | 10/1997 | Hille et al. | |
| 5,740,661 A * | 4/1998 | Yamaguchi et al. | 53/553 |
| 5,851,549 A * | 12/1998 | Svec | 424/448 |
| 5,891,290 A | 4/1999 | Derrer et al. | |
| 5,902,433 A * | 5/1999 | Becher et al. | 156/209 |
| 5,904,277 A * | 5/1999 | Niedermeyer | 223/37 |
| 5,932,240 A * | 8/1999 | D'Angelo et al. | 424/449 |
| 5,938,032 A * | 8/1999 | Svec et al. | 206/532 |
| 6,059,913 A | 5/2000 | Asmussen et al. | |
| 6,221,384 B1 * | 4/2001 | Pagedas | 424/449 |
| 6,238,362 B1 * | 5/2001 | Bracht | 602/41 |
| 6,315,854 B1 * | 11/2001 | Anhauser et al. | 156/267 |
| 6,317,629 B1 * | 11/2001 | Haak et al. | 604/20 |
| 6,461,467 B2 * | 10/2002 | Blatchford et al. | 156/230 |
| 6,464,818 B1 * | 10/2002 | Schulze et al. | 156/249 |
| 6,475,514 B1 * | 11/2002 | Blitzer et al. | 424/449 |
| 6,571,983 B1 * | 6/2003 | Schumann et al. | 221/25 |
| 6,655,112 B1 * | 12/2003 | Cremer et al. | 53/450 |
| 6,682,757 B1 * | 1/2004 | Wright | 424/448 |
| 6,791,003 B1 * | 9/2004 | Choi et al. | 602/48 |
| 6,871,477 B1 * | 3/2005 | Tucker | 53/433 |
| 6,893,656 B2 * | 5/2005 | Blitzer et al. | 424/449 |
| 7,029,549 B1 * | 4/2006 | Von Falkenhausen et al. | 156/248 |
| 7,114,422 B1 * | 10/2006 | Neuland et al. | 83/29 |
| 7,182,955 B2 * | 2/2007 | Hart et al. | 424/449 |
| 7,370,563 B2 * | 5/2008 | Neuland et al. | 83/29 |
| 2004/0253301 A1 | 12/2004 | Hille et al. | |
| 2006/0288830 A1 | 12/2006 | Neuland et al. | |
| 2008/0107719 A1 * | 5/2008 | Likitlersuang et al. | 424/449 |
| 2009/0266038 A1 * | 10/2009 | Schafer | 53/476 |
| 2010/0010418 A1 * | 1/2010 | Nisato | 604/20 |

FOREIGN PATENT DOCUMENTS

| | | |
|---|---|---|
| EP | 1 438 943 B1 | 7/2006 |

* cited by examiner

METHOD FOR THE MULTI-TRACK TAILORING OF TRANSDERMAL THERAPEUTIC PATCHES

CROSS-REFERENCE TO RELATED APPLICATION

This is a continuation-in-part application of pending international application PCT/EP2008/006678 filed Aug. 14, 2008, which claims the benefits of U.S. Provisional Application No. 60/965,616 filed Aug. 21, 2007.

BACKGROUND OF THE INVENTION

The invention relates to a method for multi-track production of transdermal therapeutic patches, with a pressure-sensitive adhesive reservoir film which comprises at least one layer and contains active substance and which is arranged between a backing film and a removable protective film.

Transdermal therapeutic patches are pharmaceutical forms that are to be applied to the skin and that look like traditional sticking plasters. The patches contain at least one pharmaceutical substance that is to be released via the skin. The pharmaceutical substances are continuously released at a predetermined rate over a fixed period of time at a defined site of application on the skin of the body.

Patches of this kind generally have simple geometric shapes. For example, they are rectangular or diamond-shaped in plan view. The patch itself is composed, for example, of a film reservoir which contains active substance and which has an adhesive layer oriented toward the skin. The adhesive layer too can additionally carry pharmaceutical substance. The film reservoir is packed between a removable protective film and a backing film that adheres to the protective film. The backing film ensures that third parties cannot take in active substances upon accidental contact with the patch.

Patches of this kind have hitherto been produced using a method known from DE 41 10 027 C2 for single-track production. In said method, the reservoir film is present as a long web which is wound up into a narrow roll. The diameter of this roll is generally many times greater than the roll width. If, in order to increase the quantity produced per unit of time on a packaging machine, several of these narrow rolls are to be used next to one another for multi-track production, the web-like reservoir films, which are sticky on one side, have to be fed synchronously to the protective film, cut to length, and transferred to the packaging device. Since the film rolls in most cases have different diameters, the web-like reservoir films are subjected to different tensile stresses, which has a negative effect on the synchronization. The synchronous feed is, however, absolutely essential to ensure that no left-over material is generated on multi-use cutting of the web-like reservoir films. Left-over material containing active substance constitutes special waste that has to be disposed of separately.

The present invention therefore addresses the problem of developing a method for multi-track production in which web-like reservoir films that can be unwound from rollers can be used without generating left-over material that contains active substance.

SUMMARY OF THE INVENTION

The present invention provides a method for the multi-track tailoring of transdermal therapeutic patches having at least a one-layer, adhesive reservoir foil containing an active ingredient, which is disposed between an adhesive back foil and a removable protective foil. The reservoir foils are applied per track with their adhesive layers on a transport element moving discontinuously in the longitudinal direction of the reservoir foils. After separating sections of the size of a patch the same are transferred to a further transport element that is moved continuously for depositing the same thereon in spaced relationship. The present invention provides a method for multi-track tailoring, wherein web-shaped reservoir foils, which can be unwound from rolls, may be utilized without producing any waste containing the active ingredient.

The method of the present invention provides here, the reservoir film for each production track is in each case wound as a reservoir film web on a roller. The reservoir film webs for each track are placed with their pressure-sensitive adhesive layer onto a conveyor element that is moved non-continuously in the longitudinal direction of the reservoir film webs. The reservoir film webs lying next to one another on the conveyor element are separated off into individual reservoir films with the aid of a separating device, transversely or obliquely with respect to the longitudinal direction and at least approximately simultaneously. The reservoir films lying next to one another in pairs at the end of the conveyor element are then transferred to a continuously moved additional conveyor element and placed at intervals thereon. The releasing conveyor element is briefly slowed down after the transfer of the front reservoir films.

BRIEF DESCRIPTION OF THE DRAWINGS

Further details of the invention will become evident from the schematically depicted illustrative embodiment, in which:

FIGS. 4 and 5 show a transdermal therapeutic patch in a plan view and in cross section. The film and layer thicknesses shown in FIGS. 4 and 5 are exaggerated, in other words they are not true to scale in relation to the length and width of the patch.

DETAILED DESCRIPTION OF THE PARTICULAR EMBODIMENTS

Figure 1:
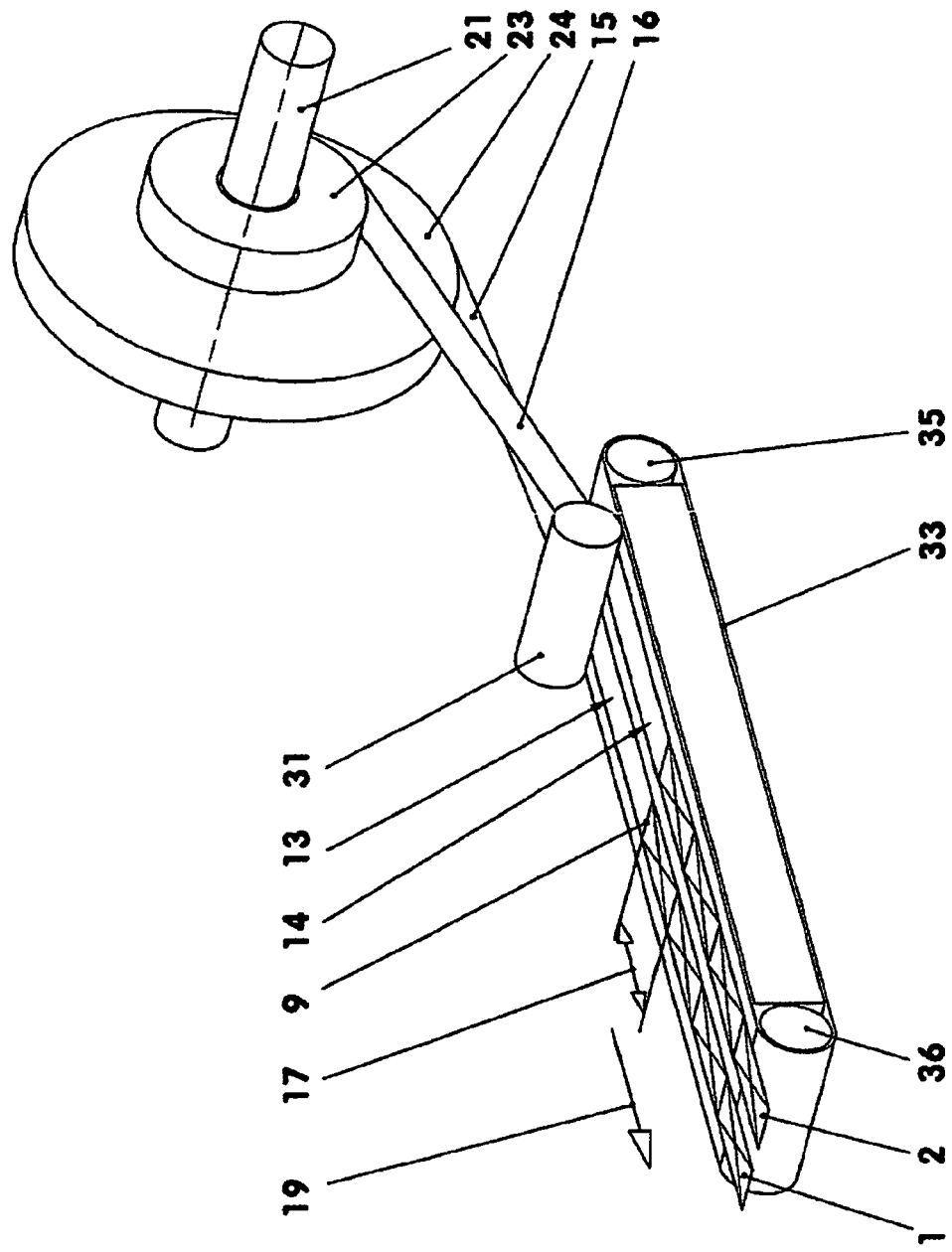
FIG. 1 shows a synchronization station, for example for two narrow rolls.

The transdermal therapeutic patch made by the present invention, principally comprises a reservoir film (1, 2) containing active substance, a protective film (5) and a backing film (6). The individual reservoir film (1, 2), in this case of rectangular shape, is composed, for example, of the active-substance-containing pressure-sensitive adhesive layer (3) and of a barrier layer (4). The latter prevents, among other things, rearward diffusion of the active substance. The laminate of pressure-sensitive adhesive layer (3) and barrier layer (4) lies centrally and adhesively on the protective film (5). The protective film (5) protrudes beyond the reservoir film (1, 2) at all the edges. The backing film (6), provided with an adhesive layer (7), lies over the reservoir film (1, 2). The adhesive layer (7) is in contact with the barrier layer (4) and the edge areas of the protective film (5). The protective film (5) and the backing film (6) enclose the reservoir film (1, 2) in a manner avoiding leakage of active substance, the protective film (5) in the illustrative embodiment protruding beyond the backing film (6).

Figure 2:
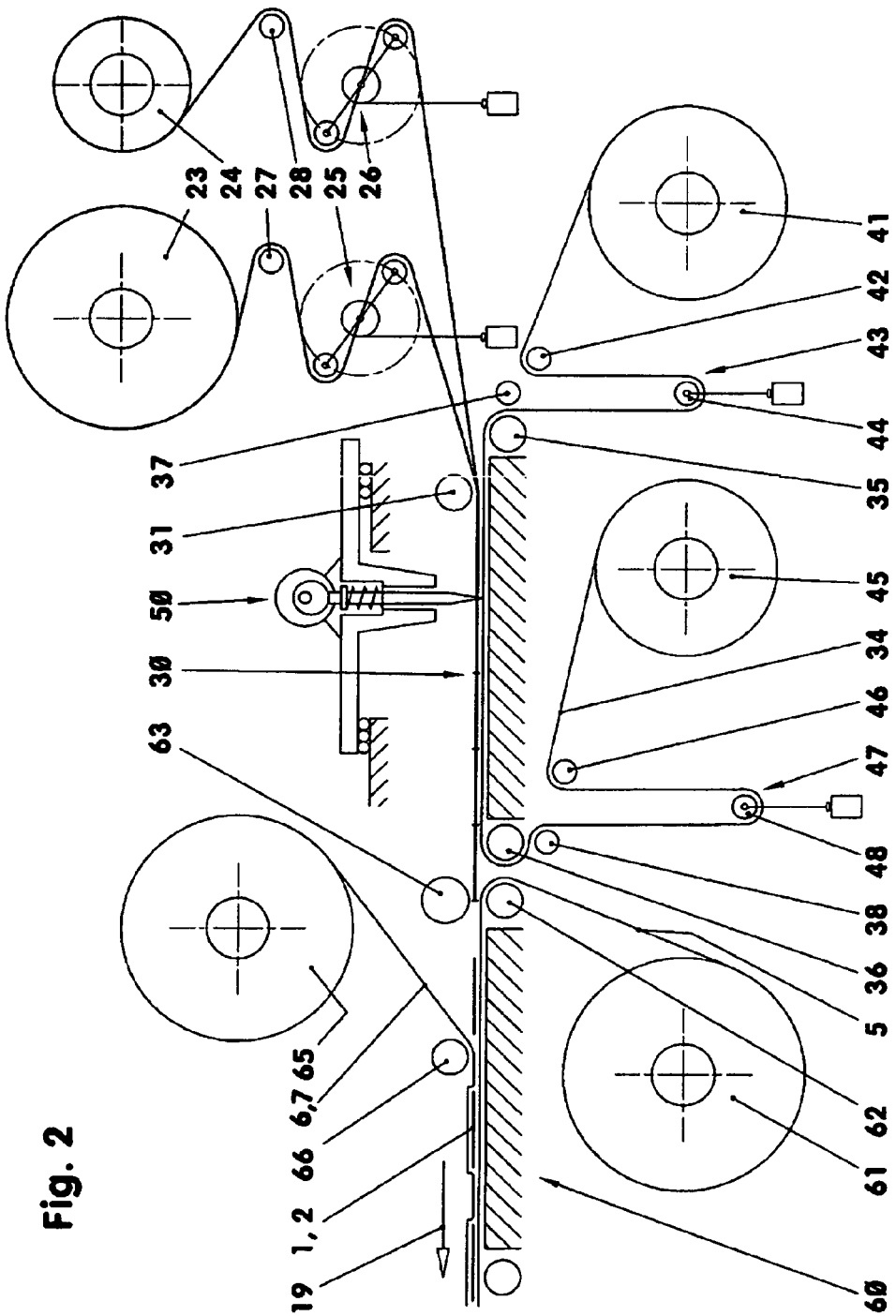
FIG. 2 shows a synchronization station with disposable conveyor film and cutting device and packaging station.
Figure 3:
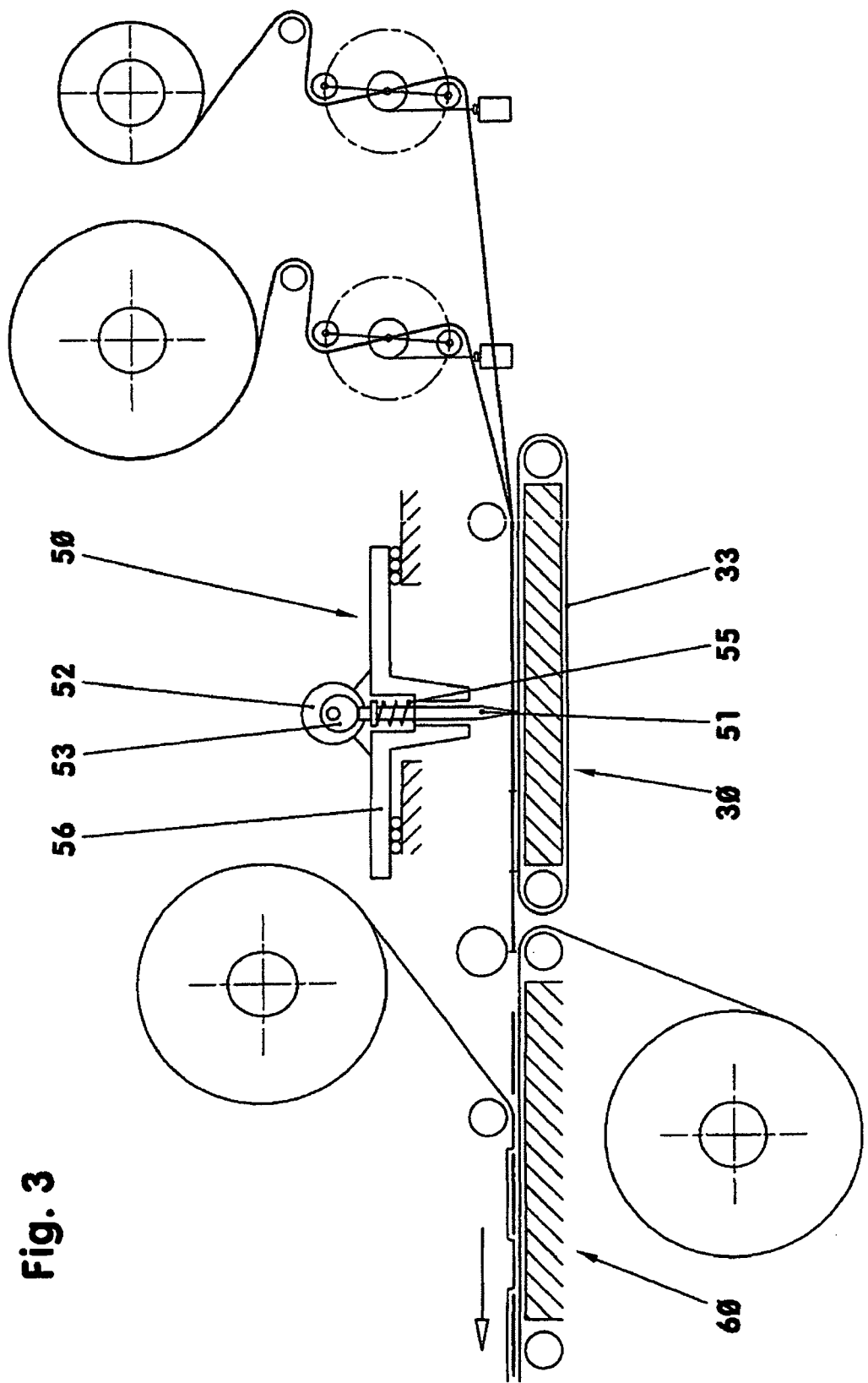
FIG. 3 is like FIG. 2, but shows a synchronization station with an endless conveyor band.
Figure 4:
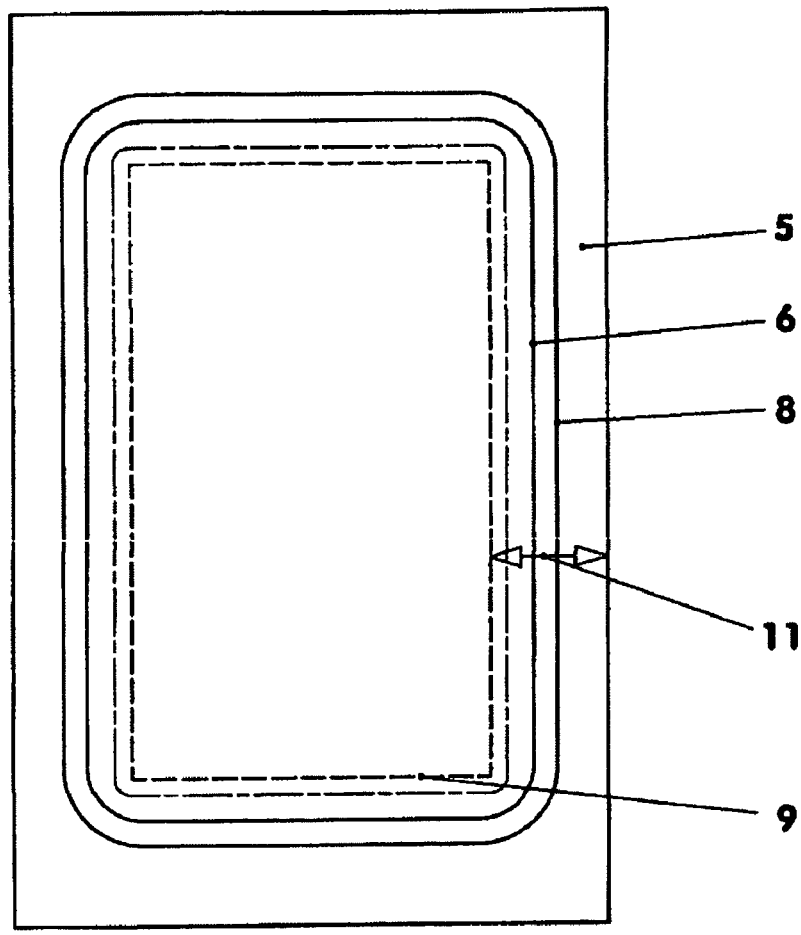
FIG. 4 shows a plan view of a finished packaged patch.
Figure 5:
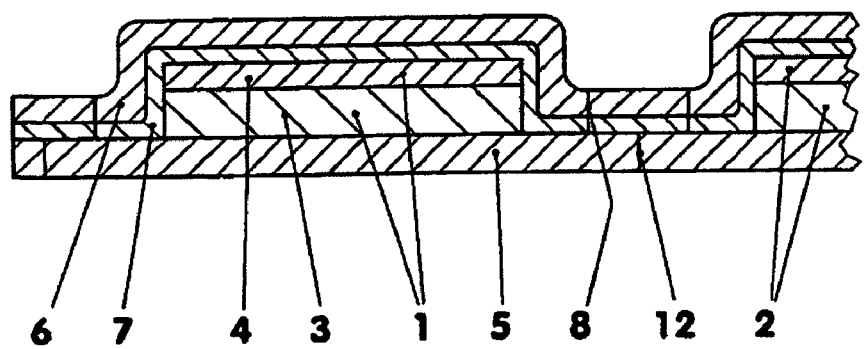
FIG. 5 shows a cross section through patches that are arranged in a row but are still unseparated.

To be able to produce such patches inexpensively, multi-use or multi-track packaging installations are necessary such as production tracks (13, 14) as shown in FIG. 1. FIGS. 1 to 3 show areas of processing stations on which some method steps for packaging of patches take place.

A first station is the synchronization station (30), cf. FIG. 1. This station comprises a conveyor element (33) guided and driven on two rollers (35, 36) for example. The conveyor element (33) is in this case a continuous conveyor band, for example a thin-walled metal film coated with fluorosilicone. Viewed in the longitudinal direction (19), the conveyor band (33) is preceded by a non-driven axle (21) on which two film rolls (23, 24) are mounted. Each film roll (23, 24) consists of a very long, narrow wound-up reservoir film web (15, 16). Since the reservoir film webs (15, 16) are also packaged or produced on single-track installations, the rolls (15, 16) in most cases have different diameters at the start of a new batch on a multi-track installation.

Each reservoir film web (15, 16) is delivered to the conveyor band (33) with the adhesive layer (3) facing downward and is placed thereon by means of the first pressure roller (31). A temporarily adhesive connection with the conveyor band (33) is obtained upon contact. The reservoir film webs (15, 16) are then conveyed synchronously and in parallel with each other only by the pulling movement of the conveyor band (33). On the conveyor band (33), the two reservoir film webs (15, 16) have a mutual spacing, which for example corresponds to twice the edge area (11) of the protective film (5). The conveyor band (33) is wider than the sum of the contiguous reservoir film webs (15, 16) including the spaces between the webs. Instead of the endless conveyor band (33), a cylindrical roller can also be used.

To simplify matters, the pendulum buffers (25, 26) from FIGS. 2 and 3 are not shown in FIG. 1.

FIG. 2 shows a conveyor element (34) which, instead of the endless conveyor band (33), provides a plastic film to be used just once. This auxiliary film (34), for example a silicone-treated polyester film, is unwound from a driven dispensing roller (41), runs through a first buffer loop (43), wraps round first and second deflection rollers (35, 36), passes a second buffer loop (47) and is finally wound back onto a driven collecting roller (45). The second deflection roller (36) generates the conveyor advance. A pressure roller (38), by virtue of its position underneath the deflection roller (36), extends the length of the arc of wrap of the plastic film (34). The buffer loops (43, 47), which with their up and down movements compensate for the intermittent movement of the auxiliary film and thus protect the drives of the rollers (41, 45) from acceleration changes, are tensioned by weight-loaded tension rollers (44, 48), for example.

Arranged above the synchronization station (30) there is a separating device (50), which is only shown schematically, cf. FIG. 3. The separating device (50) separates the respective reservoir films (1, 2) off from the corresponding reservoir film webs (15, 16) by means of a separating tool oriented here for example transverse to the longitudinal direction (19), for example a cutting knife (51). For the separating movement of the cutting knife (51), an eccentric drive or separating drive (52, 53) acts on the knife (51). The return stroke of the knife (51) is effected by a spring element (55). The cutting knife (51) and the drive (52, 53) are part of a carriage (56) which, according to the illustrative embodiment, is moved at least in some areas in synchrony with the conveyor element (33, 34) during the cutting operation.

Of course, the separating movement can also take place in the advance pause of the conveyor element (33, 34). In this case the carriage (56), without a longitudinal guide mounted on slides or rollers, stops in position relative to the synchronization station (30).

If mechanical punching or cutting tools are used for the separating operation, a compensating buffer element can be arranged between the separating drive (52, 53) and the separating tool (51) in order not to mechanically damage the corresponding conveyor element (33, 34) during the separating operation. Such an element is omitted in optical or hydraulic separating methods.

In FIGS. 2 and 3, weight-loaded pendulum buffers (25, 26) each with upstream deflection rollers (27, 28) are arranged between the film rolls (23), (24), shown here offset with respect to one another, and the upper pressure roller (31). By means of the installation of the pendulum buffers (25, 26), the for example non-driven, idle film rolls (23, 24) continue to rotate during the braking operations of the conveyor element (33, 34), such that the relatively thin reservoir film webs (15, 16) are not subjected to unnecessary tensile stress variations.

A packaging station (60) is arranged downstream of the synchronization station (30). In this packaging station (60), the protective film (5) is unwound from a for example non-driven protective film roll (61) and, after a deflection by the conveyor roller (62) is pulled in the longitudinal direction (19) with the aid of a means (not shown) generating an advance. The pressure-sensitive adhesive reservoir films (1, 2) are transferred, in this illustrative embodiment in pairs, onto the for example continuously moving protective film (5). There, they are rolled onto the protective film (5) by at least one pressure roller (63).

By matching the movements of the conveyor element (33, 34) and of the protective film (5), a constant spacing is created between the individual reservoir films (1, 2).

After the pressure roller (63), the backing film (6) is guided onto the new composite of protective film (5) and superposed reservoir films (1, 2). The backing film (6) is unwound from a for example non-driven backing film roller (65) and, with its adhesive layer (7) facing downward, is adhesively affixed to the composite (1, 2; 5) by means of the pressure roller (66).

At further stations, the edges (8) of the backing film (6) are cut and the resulting lattice-shaped remnants of backing film are pulled off. In a further step, the patches are singulated by cutting the edges (12) of the protective films.

In the illustrative embodiment, the multi-use or multi-track nature of the method is shown on the basis of a two-track installation, for example, production tracks (13, 14). Depending on the patch width, such installations can readily be converted, for example, for 10 or even more tracks.

LIST OF REFERENCE NUMBERS 1, 2 reservoir film, active substance reservoir
3 pressure-sensitive adhesive layer of (1, 2)
4 barrier layer of (1, 2)
5 protective film, removable
6 backing film
7 adhesive layer of (6)
8 edge of (6)
9 punch line of (5)
11 edge area
12 edge of protective film
13, 14 production tracks
15, 16 reservoir film web
17 reservoir film length
19 longitudinal direction, conveying direction 21 axle
23 roll, film roll, large
24 roll, film roll, small
25, 26 pendulum buffer
27, 28 deflection rollers
30 synchronization station
31 pressure roller, first, top
33 conveyor band, conveyor element
34 auxiliary film, conveyor element
35 deflection roller, first
36 deflection roller, second, driven
37, 38 pressure rollers, bottom
41 dispensing roller
42 deflection roller
43 buffer loop, first
44 tensioning roller
45 collecting roller
46 deflection roller
47 buffer loop, second
48 tensioning roller
50 separating device
51 cutting knife, knife, separating tool
52 motor, part of separating drive
53 eccentric, part of separating drive
55 spring element, restoring spring
56 carriage
60 packaging station
61 protective film roller
62 conveyor roller
63 pressure roller
65 backing film roller
66 pressure roller

What is claimed is:

1. A method for multi-track (13, 14) production of transdermal therapeutic patches comprising a pressure-sensitive adhesive reservoir film (1, 2) which comprises at least one layer of a pressure-sensitive adhesive layer (3) containing active substance and is arranged between a backing film (6) and a removable film (5), said method comprising the steps:

the reservoir film (1, 2) for each production track (13, 14) is in each case wound as a reservoir film web (15, 16) on a roller (23, 24);

the reservoir film webs (1, 2) for each track (13, 14) are placed with their pressure-sensitive adhesive layer (3) onto a conveyor element (33, 34) that is moved non-continuously in the longitudinal direction (19) of the reservoir film webs (15, 16);

all the reservoir film webs (15, 16) lying next to one another on the conveyor element (33, 34) are separated off into individual reservoir films (1, 2) with the aid of a separating device (50), transversely or obliquely with respect to the longitudinal direction (19) and at least approximately simultaneously;

the reservoir films (1, 2) each lying next to one another at the end of the conveyor element are transferred to said removable protective film (5), which is moved continuously to convey the reservoir films (1, 2) and to place the reservoir films (1, 2) at intervals thereon;

the conveyor element (33, 34) is briefly slowed down after the transfer of the reservoir films (1, 2).

2. The method as claimed in claim 1, wherein the production tracks (13, 14) are arranged to extend parallel to one another.

3. The method as claimed in claim 1, further comprising the step of the individual reservoir film webs (15, 16) of the corresponding production tracks (13, 14) are pressed jointly onto the conveyor element (33, 34) by a first pressure roller (31).

4. The method as claimed in claim 3, further comprising the step of the individual reservoir film webs (15, 16) are deflected several times between the film rollers (23, 24) and the pressure roller (31) with the aid of film buffers (25, 26).

5. The method as claimed in claim 1, further comprising the step of both conveyor elements (33, 34; 5) have the same speed of advance in the common phase of movement.

6. The method as claimed in claim 1, further comprising the step of the separating device (50) is arranged on a carriage (56) mounted on rollers or slides and is moved together with the carriage (56) in parallel and in some areas in synchrony with the conveyor element (33, 34).

7. The method as claimed in claim 6, further comprising the step of, after the transfer of the reservoir films (1, 2) to the conveyor element (5), the separating device (50) travels back an average reservoir film length (17), with the conveyor element (33, 34) stationary, in order to begin with a new separating operation and a new advance movement of the conveyor element (33, 34).

8. The method of claim 1, further comprising the step of the reservoir films (1, 2) are rolled onto said removable protective film (5) at intervals thereon by at least one second pressure roller (63).

9. The method of claim 8, further comprising the step of a backing film (6) having a downwardly facing adhesive layer (7) is guided onto the new composite of said removable protective film (5) and superposed reservoir films (1, 2) and is adhesively affixed to the composite (1,2;5) by means of a third pressure roller (66).

10. The method of claim 9, further comprising the step of cutting backing film (6) to form edges (8) and lattice shaped remnants and removing the lattice shaped remnants.

11. The method of claim 10, further comprising the step of the patches are singulated by cutting the edges (12) of said removable protective film (5).

* * * * *